United States Patent [19]

Schmid et al.

[11] Patent Number: 4,671,900
[45] Date of Patent: Jun. 9, 1987

[54] PREPARATION OF LIGHT-COLORED, WASH ACTIVE α-SULFOFATTY ACID

[75] Inventors: Karl Schmid, Mettmann; Werner Stein, Düsseldorf-Unterbach; Horst Baumann, Leichlingen, all of Fed. Rep. of Germany

[73] Assignee: Henkel Kommanditgesellschaft auf Aktien, Düsseldorf-Holthausen, Fed. Rep. of Germany

[21] Appl. No.: 288,769

[22] Filed: Jul. 31, 1981

[30] Foreign Application Priority Data

Dec. 19, 1980 [DE] Fed. Rep. of Germany ....... 3047897

[51] Int. Cl.<sup>4</sup> .......................................... C07C 143/90
[52] U.S. Cl. .................................................... 260/400
[58] Field of Search ........................................ 260/400

[56] References Cited

U.S. PATENT DOCUMENTS

| 2,195,187 | 3/1940 | Moyer | 260/400 |
| 3,158,632 | 11/1964 | Blaser et al. | 260/400 |
| 3,256,303 | 6/1966 | Stein et al. | 260/400 |
| 3,354,187 | 11/1967 | Stein et al. | 260/400 |
| 3,420,858 | 1/1969 | McCrimlisk | 260/400 |
| 3,452,064 | 6/1969 | Stein et al. | 260/400 |
| 3,485,856 | 12/1969 | Wulff et al. | 260/400 |
| 4,080,372 | 3/1978 | Stein et al. | 260/400 |

Primary Examiner—Charles F. Warren
Attorney, Agent, or Firm—Hammond & Littell, Weissenberger & Dippert

[57] ABSTRACT

This invention is directed to the preparation of α-sulfofatty acid esters. More particularly, this invention is directed to a process for the simplified preparation of light-colored, wash-active esters of α-sulfofatty acids with monovalent $C_1$ to $C_8$ alcohols or their salts from fats and oils of vegetable and/or animal origin comprising re-esterification with the monovalent alcohols or saponification and esterification with the monovalent alcohols, separation of the fatty acid ester formed, hydrogenation of the fatty acid ester, sulfonation, and bleaching, wherein a fatty acid ester fraction from which accompanying fatty acid glycerides have been removed to the extent of about 1 percent by weight or less, based upon the weight of the material to be sulfonated, is introduced into the sulfonation stage.

56 Claims, No Drawings

PREPARATION OF LIGHT-COLORED, WASH ACTIVE α-SULFOFATTY ACID

FIELD OF THE INVENTION

This invention is directed to the preparation of α-sulfofatty acid esters. More particularly, this invention is directed to the simplified preparation of light-colored, wash-active α-sulfofatty acid esters by use of fats and oils of vegetable and/or animal origin.

BACKGROUND OF THE INVENTION

This invention is based upon the general problem of simplifying the known preparation of wash-active α-sulfofatty acid esters from fats and oils, particularly those of natural origin, in such a way that the fatty acids or fatty acid mixtures of vegetable and/or mineral origin can be used as a feasible alternative in the production of modern detergent compositions, thus making it reproducible for large scale technical purposes. In the field of washing and cleaning agents, particularly fabric detergents, the emphasis today is, as is known, on petroleum-based synthetic products although it has been known for decades that high-grade wash-active components can also be obtained from, in particular, the fatty acid triglycerides of natural starting materials.

Thus, U.S. Pat. No. 2,195,187, incorporated herein by reference, describes α-sulfofatty acids and their esters as wash-active substances. They are obtained by sulfonation of lower alkyl esters of saturated higher fatty acids with sulfur trioxide. The lower fatty acid alkyl esters used as starting materials are obtained by re-esterification of hydrogenated fats and oils with monovalent lower alkanols, particularly methanol.

Scientists of Henkel KGaA have dealt intensively in later studies with this class of wash-active α-sulfofatty acids and corresponding fatty acid esters, as well as their salts. U.S. Pat. No. 3,256,303, incorporated herein by reference, for example, describes a process for the production of this class of compounds. Fatty acids and fatty acid esters, which contain from 6 to 28 carbon atoms in the fatty acid radical, which have no other sulfonatable or sulfatizable groups, apart from the α-position carbon atom of the fatty acid radical, and which have an iodine number less than 5, are sulfonated with a sulfur trioxide-inert gas mixture, and the reaction product is neutralized. A parallel process for the production of the same compounds, working with alternate process conditions but at the end with the same means, is described in U.S. Pat. No. 3,158,632, incorporated herein by reference.

One of the main difficulties in this field is the color-instability of the fatty acid-containing starting material in the sulfonation stage. Dark black-brown crude products are obtained, which products must be worked up to light-colored products for use in washing and cleaning agents. The color of the crude sulfonation products depends to a certain extent on the working conditions. However, the technical utilization of this interesting possibility of the raw material is prevented by the following fact: the higher the yield in the sulfonation stage is, the darker is the reaction product and the greater are the difficulties of obtaining light-colored end products.

To reduce this difficulty, and to in particular improve the control of the sulfonation reaction while avoiding overheating, which can lead to undesired discolorations and secondary reaction, German Published Application (DOS) No. 12 62 265, incorporated herein by reference, suggests the sulfonation of mixtures of from 25 to 95 percent by weight of alkyl benzenes and from 5 to 75 percent by weight of saturated fatty acid esters. Here considerable quantities of alkyl benzenes used as reactive diluters are supposed to overcome the color difficulties.

The importance of the constitution of the fatty acids or fatty acid mixtures to be sulfonated is well known in the art. It is particularly required that the fatty acids to be sulfonated in α-position contain no, or only a few, double bonds, as well as no other reactive groups—especially no hydroxyl groups. By selection of suitable oils or fats, this problem is confined to the elimination of unsaturated bonds in the fatty acid molecule. These defects are eliminated by extensive hydrogenation of the starting material prior to sulfonation. The literature of the state of the art requires iodine numbers less than 5, preferably less than 2. In practice, far lower iodine-numbers, for example, in the range of from about 0.1 to 0.3, are used.

The separation of interfering accompanying substances from the fatty acids of fatty acid esters to be sulfonated is likewise required to reduce the discoloration problem. With respect to fatty acids and fatty acid esters used as a starting material, it is recommended to start from distillates (see, for example, U.S. Pat. No. 3,158,632, Col. 3, second paragraph). If distillation is not possible, for example, with triglycerides, other purifications steps are recommended for removing albuminous and slimy substances.

Bleaching of the crude sulfonic acid derivatives has always been required as the last step. Two particular methods are generally known to the art: acid bleaching with hydrogen peroxide (see, U.S. Pat. No. 3,159,657, incorporated herein by reference), and combination bleaching, where an acid hydrogen peroxide bleaching stage is followed by neutralization of the sulfonic and partly bleached material, followed again by bleaching with hydrogen peroxide, or better with hypochlorite (see, U.S. Pat. No. 3,452,064, incorporated herein by reference).

Special difficulties or problems, regarding discolorations occur when the sulfonation is to be increased to yields of over 90% or even to sulfonation degrees of over 95%, which problems are dealt with extensively in U.S. Pat. No. 3,485,856, incorporated herein by reference. According to this patent sulfur trioxide has a highly disintegrating effect on saturated fatty acid esters which are free of alcoholic hydroxyl groups, which leads unavoidably to deep-dark discolored sulfonation products in the production of highly sulfonated products with a degree of sulfonation of at least 90%, preferably at least 94%, and particularly at least 96%.

The increase in the degree of sulfonation in these ranges is not only of interest for economic reasons, however, since other factors require such high degrees of sulfonation too. Ester sulfonates with a corresponding low degree of sulfonation lead to difficulties in the conventional production of detergent compositions by spray drying. High pluming values appear in the processing of these ester sulfonates. Furthermore, the degree of sulfonation of ester sulfonates is directly related to an undesired by-product formed in this reaction, namely, α-sulfofatty acid. This compound, which is present after neutralization as a disodium salt, is poorly water-soluble and is therefore unsuitable as a raw material for detergents. Increasing the degree of sulfonation from 90% to 96% in these ester sulfonates causes, for example, a decrease of this undesired by-product from 25% to 16%.

U.S. Pat. No. 3,485,856, which deals with the last-mentioned problem, suggests that to limit the discoloration and to maintain certain temperatures in the sulfonation reaction, water should be introduced into the sulfonation product in such quantities that sulfuric acid is formed from the existing excess sulfur trioxide and the water, the concentration of the $H_2SO_4$ being in the range of from about 20 to 100 percent by weight at the start of the following bleaching phase.

For the large-scale technical process, however, new difficulties arise, which represent a considerable risk source. The viscosity of the sulfonation product is greatly influenced in the high acid range by even very small amounts of water. The addition of 2% hydrogen peroxide in the form of a 35% solution—with the required amounts of water—to the crude sulfonation product with a $C_{16}/C_{18}$-chain length, leads to a sharp viscosity rise. In the continuous technical process, this involves the risk that the pipe line will be clogged. This viscosity rise is particularly critical with an addition of from 1.8 to 2.5 percent by weight of hydrogen peroxide, based upon the weight of the crude sulfonic acid.

This characteristic of the crude sulfonating product resulting in technical difficulties is also the reason that bleaching with hydrogen peroxide leads to considerable difficulties in the acid range, at least in fatty acid alkyl esters with $C_{16}/C_{18}$-chain lengths, as they can be obtained from, for example, tallow and palm oil. If fatty acid methyl esters, obtained by re-esterification or esterification, are sulfonated for from about 10 to 90 minutes at temperatures of from about 70° to 130° C., about 95% of deep-black reaction products are obtained at the desired degrees of sulfonation. The use of these products as a raw material for detergents requires bleaching. Bleaching in the alkaline medium with hydrogen peroxide or sodium hypochlorite does not lead to satisfactory results. Even sodium hypochlorite in amounts of 3 percent by weight—based upon the weight of wash-active substance—leads only to Klett dye numbers in the range of 140. Larger amounts of sodium hypochlorite can no longer be used, however, since the sodium chloride formed in this bleaching reaction leads to unacceptable thickening of the neutralized ester sulfonate paste. Nor are Klett dye numbers in the purified product which are over 50 to 60 acceptable. Incompletely bleached ester sulfonates give rise to the risk of becoming darker. Color constancy is, however, absolutely necessary for spray-drying when this surfactant is used in detergents.

The best bleaching method for crude ester sulfonates so far is the use of hydrogen peroxide in a highly acid range (pH=0), the bleaching effect being particularly pronounced. However, such a procedure involves the risk of the above-described sudden viscosity increase. With highly sulfonated ester sulfonates, even 2 percent by weight of hydrogen peroxide is not enough to bring the Klett dye number to 50.

After neutralization of the crude sulfonic acid, it is therefore necessary to bleach again with sodium hypochlorite. A reduction in the amount of the bleaching agent with a simultaneous increase of the bleaching time leads to less favorable colors. The use of hydrogen peroxide in large quantities has, in addition, the effect that bleaching with from 0.5 to 1 percent by weight of sodium hypochlorite can only be possible after the decomposition of the hydrogen peroxide which had not reacted in the bleaching reaction, which takes about 24 hours. If hydrogen peroxide is still present, sodium hypochlorite has a greatly reduced bleaching effect.

There are also a number of other difficulties. Due to the great viscosity increase with the addition of 2 percent by weight of hydrogen peroxide, for example, to the crude sulfonic acid, it is not possible to obtain paste concentrations higher than 28 percent by weight of wash-active substance. In this bleaching method there are also problems with foaming, which are technically difficult to control, in particular, the foam introduced into the crude sulfonic acid leads to a further viscosity increase.

The many difficulties appearing in the various stages of the total process lead according to our present knowledge to a forced compromise between sulfonation and bleaching. The optimum degree of sulfonation obtainable in practice are about 90%.

OBJECTS OF THE INVENTION

It is an object of the invention to provide a process for the preparation of α-sulfofatty acid esters.

It is also an object of the invention to provide a process for the simplified preparation of light-colored, wash-active α-sulfofatty acid esters by use of fats and oils of vegetable and/or animal origin.

It is an additional object of the invention to provide a procedure whereby degrees of sulfonation higher than 90%, especially higher than 95%, are possible.

It is a further object of the invention to provide by means of a technically safe procedure light-colored, bleached end products with Klett dye numbers under about 50.

It is a yet further object of the invention to provide a procedure which is generally applicable to naturally occurring fatty acids and which especially permits the safe processing of $C_{16}/C_{18}$-fractions.

These and other objects of the invention will become more apparent from the discussion below.

DETAILED DESCRIPTION OF THE INVENTION

The subject of the present invention is therefore, in a first embodiment, a process for the simplified preparation of light-colored, wash-active esters of α-sulfofatty acids with monovalent $C_1$ to $C_8$ alcohols (α-sulfofatty acid esters) or their salts from fats and oils of vegetable and/or animal origin by re-esterification with the monovalent alcohols or saponification and esterification with the monovalent alcohols of the fats or oils, which can be hardened if desired by hydrogenation, separation of the fatty acid ester fraction formed, hydrogenation of the fatty acid ester fraction as far as necessary that is, sufficient to effect complete saturation of double bonds, subsequent sulfonation, and bleaching of the crude sulfonation product, this process being characterized in that a fatty acid ester fraction is introduced into sulfonation stage from which the accompanying fatty acid glycerides have been removed, with the proviso that there is a residual content of fatty acid glycerides of not more than about 1 percent by weight, based upon the weight of the material to be sulfonated.

The invention is based on the surprising finding that it requires the fatty acid ester to undergo a certain purification step before being introduced into the sulfonation stage to avoid excessive discoloration at high degrees of sulfonation with subsequent difficulties in bleaching. More specifically, if the natural triglycerides of vegetable and/or animal origin are subjected in conventional large-scale technical processes to re-esterification with monofunctional alcohols or to lipolysis and subsequent esterification with these alcohols, a fatty acid alkyl ester is obtained as a main fraction which, despite distillation, still contains a small amount of accompanying glycerides. ("Accompanying glycerides" in the present definition are mono-, di-, and/or triglycerides of those fatty acids of fatty acid mixtures which have been converted as the main product to the monoalkyl ester but which are still present in a residual amount in the form of these glycerides as accompanying impurities in the material to be sulfonated.) The content of these accompanying glycerides is usually of the order of from about 2 to a maximum of 5 percent by weight, generally from about 2 to 3 percent by weight, based on the weight of the fatty acid ester fraction. One can imagine various possibilities as to how such a glyceride content might be carried over into the product despite distillation of the main fraction, but clarification of this question is not essential for the invention.

Rather, what is determinant is that it was recognized that this low content of accompanying glycerides plays an obviously disproportional role in the formation of the undesired strong discoloration during the sulfonation reation. Thus it was surprisingly found that the partial, preferably predominant, removal of these accompanying glycerides leads to such a reduction of the discolored by-products in the sulfonation reaction that a technical solution to the above-described problem of discoloration is now possible.

The maximum residual content of the accompanying glycerides in the fatty acid ester fraction to be used in the sulfonation stage is about 1 percent by weight, based upon the weight of the fatty acid ester fraction. It is preferred to work with residual contents of the accompanying glycerides of not more than about 0.5 percent by weight, particularly not more than about 0.3 percent by weight. Even lower residual contents of the accompanying glycerides can be used, for example, 0.2 or even 0.1 percent by weight. Preferably the accompanying glycerides are completely removed. Dependent upon the parameters of the process according to the invention to be described below, and particularly upon the nature of the vegetable and/or animal natural product used as a first starting material, a solution of the above-described problem is possible by determining and setting the maximum admissible residual content of the accompanying glycerides.

The reduction and control of the admissible residual content of the accompanying glycerides is possible, particularly by distillation. If the control of this content of interfering glycerides is effected by distillation, the following applies: while the conventional technological process, the distillative separation of the reaction product from the fat or oil re-esterification with monofunctional alcohols leads to the above described admixture of the accompanying glycerides, the glycerides can be separated from this fraction by a second distillation. A satisfactory separation for the purposes of the invention can already be achieved by simple overhead distillation. If, for example, a corresponding fatty acid ester fraction is involved, the desired purification can be effected by overhead distillation at a sump temperature of up to 280° C./1 mbar. If desired, a greater separating effect can be achieved by using a fractioning zone. That at least a substantial separation of the accompanying glycerides is possible in this second distillation, while the above-described admixture of the accompanying glycerides is the usual result in the first distillation, may be due to the fact that free glycerin is always present in the first distillation stage from the fat or oil cleavage or re-esterification since glycerin is only incompletely removed from the re-esterification product by the usual washing with water The crude $\alpha$-sulfofatty acid ester product obtained from the subsequent sulfonation is bleached to the desired light-colored end product. The bleaching is preferably effected with hydrogen peroxide or hydrogen peroxide supplying compounds and/or sodium hypochlorite. In the process according to the invention, it is possible to effect the bleaching with only one of the above-mentioned bleaches, or to use a combination treatment.

1. Bleaching method

Alkaline bleaching method with sodium hypochlorite

The crude sulfonic acid of the ester sulfonate is neutralized as usual, in accordance with procedures described in the patents mentioned above. Since ester sulfonate pastes with a pH of less than 6 become highly viscous, while at a pH of over 10 there is a risk of ester splitting, the neutralization is preferably effected by simultaneous continuous combination of crude acid and soda lye in a pH-range of from about 6.5 to 10. For bleaching with sodium hypochlorite there are two possibilities:
(a) The alkalinity of the sodium hypochlorite soluton is already used in the neutralization. Here the neutralization is thus effected by continuous simultaneous combination of sodium hydroxide solution, crude sulfonic acid, and sodium hypochlorite solution, preferably in a pH range of from about 7 to 9; and
(b) The crude sulfonic acid is first neutralized and then bleached with sodium hypochlorite.

The amount of sodium hypochlorite required for a Klett dye number of 50 or less is from about 0.1 to 3 percent by weight of sodium hypochlorite, based upon the weight of the material to be bleached, dependent upon the extent of the preliminary purification according to the invention. Normally the amount of sodium hypochlorite is from about 1 to 3 percent by weight, about 2 to 3 percent by weight being particularly advisable. The use of larger quantities of sodium hypochlorite is not impossible, but such use may cause technical difficulties since the resulting amount of common salt, i.e., sodium chloride, can lead to considerable thickening of the ester sulfonate paste.

The temperature of the hypochlorite bleach is preferably in a range of from about 50° to 70° C., particularly from about 55° to 65° C. The bleaching treatment generally takes from about 1 to 10 hours, preferably from about 2 to 4 hours. The optimum bleaching treatment to obtain a Klett dye number of 50 or less is about 3 hours at 60° C.±5° C.

Higher temperatures lead to color deteriorations, lower temperatures require longer bleaching times. A great advantage of this bleaching is that the products with a Klett dye number of 50 are sufficiently color-stable in further processing. Thus, for example, a material prepared as indicated above had a Klett dye number of 40 (bleaching of ester sulfonate paste at 60° C./3 hours), while after storage for 24 hours at 60° C., the Klett dye number had only increased to 42. Incompletely bleached ester sulfonate pastes are not color-stable, however, and the rate of increase of the Klett dye number is directly related to the color value achieved during bleaching.

Another advantage of the bleaching method described here is that it permits for the first time obtaining ester sulfonate pastes with a content of wash-active substance of over 28 percent by weight. Thus, it is possible, for example, to obtain contents of wash-active substance in the range of from about 30 to 40 percent by weight.

2. Bleaching method

Acid bleaching method with hydrogen peroxide or combination method

The separation of the accompanying fatty acid glycerides from the fatty acid ester fraction to be sulfonated according to the invention permits the use of limited quantities of hydrogen peroxide, where both the sole use of hydrogen peroxide and its combination with a subsequent second bleaching step, particularly with sodium hypochlorite, is possible. The hydrogen peroxide bleaching is effected in the acid range. Preferably the crude sulfonation product is mixed directly with hydrogen peroxide. In the preferred embodiment of this bleaching method, less than 2 percent by weight of hydrogen peroxide is used, calculated as 100% hydrogen peroxide, based upon the crude sulfonation product. Amounts of up to about 1.5 percent by weight of hydrogen peroxide, and particularly those in the range of from about 0.5 to 1.5 percent by weight, are preferred.

The process according to the invention permits obtaining Klett dye numbers in the desired range solely by treating the crude sulfonation product with hydrogen peroxide. It is advantageous to work, for example, with about 1 percent by weight of hydrogen peroxide, based upon the weight of the crude sulfonation product, calculated as 100% hydrogen peroxide. The problems of foaming and of residual hydrogen peroxide amounts after bleaching are clearly reduced. The production of substantially salt-free ester sulfonate pastes is possible. This in turn has a favorable effect on the adjustable solid contents in the finished product.

The combined use of hydrogen peroxide and hypochlorite can be particularly effective. Thus the crude sulfonation product can be pre-bleached in a first stage with from about 0.5 to 1.5 percent by weight, particularly with about 1 percent by weight, of hydrogen peroxide (calculated as 100% material), followed by a second bleaching with from about 0.5 to 1.5 percent by weight, particularly with about 1 percent by weight, of sodium hypochlorite. For bleaching with sodium hypochlorite, the procedures given above under category 1 are applicable.

Details for carrying out the acid bleaching or the multistage combination bleaching can be found in the above mentioned U.S. Pat. Nos. 3,159,657, 3,452,064, and 3,485,856. Thus, hydrogen peroxide bleaching is not effected above about 100° C. and below about 80° C. The bleaching time varies with the starting material, the amount of hydrogen peroxide, and the temperature. It can vary from about 15 minutes to several hours, for example, from about 5 to 10 hours.

Specifically, certain facts known to those skilled in the art is applicable to carrying out various stages of the entire process according to the invention. These facts are set forth briefly herebelow:

The oils and/or fats used as starting materials can originate from plants or from land or water animals. Their fatty acid radicals primarily contain from about 8 to 18 carbon atoms, fats with from about 10 to 14 carbon atoms in the fatty acid radicals being equally suitable as those with from about 16 to 18 carbon atoms in the fatty acid radicals. Sulfatizable or sulfonatable groups, which should not be present in these fatty acids or their esters—apart from the $\alpha$-position hydrogen atom of the fatty acid radical—include, for example, double bonds or alcoholic hydroxyl groups. Double bonds present in the starting material can be removed, that is saturated, by hydrogenation. It is possible to effect this hydrogenation in the starting fat or oil material, but preferably the fatty acid alkyl ester obtained after glyceride splitting is saturated by hydrogenation. This hydrogenation is effected in known manner. The hydrogenation products should have iodine numbers less than 2, preferably less than 1, and particularly in the range of about 0.5 and less. Preferred starting materials for the subsequent sulfonation are tallow fatty acid methyl esters and palm oil fatty acid methyl esters.

The separation of the accompanying fatty acid glycerides from the ester of the fatty acids with the monofunctional alochols can be effected before or after the hydrogenation of these fatty acid esters. Preferably the accompanying fatty acid glycerides are removed after the hydrogenation of the fatty acid alkyl ester.

The material prepared this way is then sulfonated in known manner, for example, at temperatures of from about 70° to 130° C. in a falling film reactor with a mixture of gaseous sulfur trioxide and inert gas during a period of from about 10 to 90 minutes. The degree of sulfonation is preferably more than 90%, particularly more than 92%, and as a rule more than 94%, sulfonation degrees of 95% and over being particularly preferred.

The subsequent bleaching is effected in accordance with one of the above indicated procedures. Klett dye numbers under 60, and particularly up to 50, are obtained according to the invention. The bleached material can be neutralized—if necessary—to a neutral paste of the pH-range of from about 7 to 9, especially from about 7.5 to 8.5.

The following examples are intended to illustrate the invention and should not be construed as limiting the invention thereto. Quantity percentages are in terms of percent by weight unless stated otherwise.

COMPARISON EXAMPLE 1

A tallow fatty acid methyl ester, obtained by re-esterification of tallow with methanol and subsequent distillation and hardening, was used as charging material. This material had the following characteristics:

Iodine number: 0.3
Hydroxyl number: 1.1
Acid number: 0.5
Saponification number: 195.8

Five hundred seventy-three grams (approximately=2 mols) of the above-described material were sulfonated in a standing cylinder heated to 80° C. by passing-in for 65 minutes of a 5 percent by volume $SO_3$/air mixture which contained a total of 208 gm (=2.6 mols) of $SO_3$, with an after-reaction time of 15 minutes. The amount of crude sulfonic acid thus obtained, which had a degree of sulfonation of 98%, was divided into halves. One half was neutralized immediately by simultaneously combining crude sulfonic acid and soda lye in a pH-range of from 6.5 to 8 to form an aqueous paste containing about 25 percent by weight of sulfonation product, which was subsequently bleached for one hour at 60° C. with 15.4 or 23.1 percent by weight of a 13% aqueous NaOCl solution, based upon the weight of the sulfonation product. A 5 percent aqueous solution, based upon the sulfonation product, adjusted to pH 7, as measured in the Klett photometer [(Model 800-3 by Klett-Summerson) with blue filter (420 mm) in a Klett-round glass cuvette] had Klett dye numbers of 210 and 180, respectively.

The other half was treated as follows: The crude sulfonic acid was first bleached for 15 minutes at 55° C. by the addition of 2.86 percent by weight of a 35% aqueous $H_2O_2$ solution, subsequently neutralized as described above with soda lye, and bleached for one hour at 60° C. with 7.69 percent by weight of a 13% aqueous NaOCl solution, based upon the sulfonation product. The paste thus obtained had a Klett number of 130 (5% sulfonation product, blue filter, pH 7).

COMPARISON EXAMPLE 2

A tallow fatty acid methyl ester prepared in a manner similar to that in Comparison Example 1 was hardened again and had the following characteristics:
Iodine number: 0.08
Hydroxyl number: 1.1
Acid number: 0.4
Saponification number: 195.8

This material was sulfonated as described in Comparison Example 1 (degree of sulfonation—98%), neutralized, and bleached, using for one half of the material bleached only NaOCl as a bleach and for the other half a combination of $H_2O_2$ and NaOCl. The Klett dye numbers thus obtained were 220 (2 percent by weight of NaOCl), 160 (3 percent by weight of NaOCl), and 160 (1 percent by weight of $H_2O_2$ and 1 percent by weight of NaOCl). The percentages of the bleaching agent are based upon the sulfonation product, whereby the bleaching agent is calculated as 100%.

EXAMPLE 1

Three hundred twenty kilograms of a tallow fatty acid methyl ester prepared as in Comparison Example 1 were further distilled, with 309 kg passing over as distillate under conditions comprising a sump temperature of up to 246° C./1 mbar. The residue of 3.4 percent by weight of the charged material consisted primarily of mono-, di-, and triglycerides of the fatty acids present in the tallow. Three percent by weight of this residue was identified as hydroxysteric glyceride and hydroxyoleic glyceride.

The tallow fatty acid methyl ester distillate (iodine number: 0.3; hydroxyl number: 0.7; acid number: 0.7; saponification number: 196) was sulfonated in accordance with the procedure described in Comparison Example 1 (degree of sulfonation—98%) and bleached. The Klett numbers obtained were 96 (2 percent by weight of NaOCl) and 55 (3 percent by weight of NaOCl) and 35 (1 percent by weight of $H_2O_2$ and 1 percent by weight of NaOCl), respectively.

COMPARISON EXAMPLE 3

A tallow fatty acid methyl ester obtained by splitting the tallow and washing out the glycerin, followed by distillation and esterification of the tallow fatty acid, with subsequent hardening was employed as starting material. The resulting tallow fatty acid methyl ester (iodine number: 0.4; hydroxyl number: 1.1; acid number: 0.4; saponification number: 195) was sulfonated according to the procedure described in Comparison Example 1 (degree of sulfonation—96%) and bleached. The Klett numbers obtained with a bleaching time of 1 hour at 60° C. were 125 (2 percent by weight of NaOCl), 90 (3 percent by weight of NaOCl), and 68 (1 percent by weight of $H_2O_2$ and 1 percent by weight of NaOCl), respectively, whereby the bleaching agent is calculated as 100% and the percentages by weight are based upon the content of the sulfonated product.

EXAMPLE 2

The charging material described in Comparison Example 3 was purified additionally by distillation, as described in Example 1, and a distillation residue of 2.3 percent by weight was obtained. An amount of 1.8 percent by weight of this residue was identified as hydroxystearic glyceride and hydroxyoleic glyceride.

The distillate (iodine number: 0.3; hydroxyl number: 1.1; acid number: 0.4; saponification number: 195) was sulfonated in the same manner as in Comparison Example 1 (degree of sulfonation—96%), and bleached. The Klett numbers obtained with a bleaching time of 1 hour at 60° C. were 52 (2 percent by weight of NaOCl), 40 (3 percent by weight of NaOCl), and 18 (1 percent by weight of $H_2O_2$ and 1 percent by weight of NaOCl), respectively, whereby the bleaching agent is calculated as 100% and the percentages by weight are based upon the content of sulfonated product.

EXAMPLE 3

To the charging material described in Example 1—a tallow fatty acid methyl ester distillate—were added 1 percent by weight of each of behenic acid methyl ester, glycerin monostearate, and glycerin tristearate. This mixture was again sulfonated as described in Example 1 (degree of sulfonation—96%) and bleached. After a bleaching time of 1 hour with sodium hypochlorite, pastes with a content of sulfonated product of 26 percent by weight were obtained. The Klett numbers were 43 (2 percent by weight of NaOCl) and 30 (3 percent by weight of NaOCl), respectively.

EXAMPLE 4

Two percent by weight of glycerin tristearate were added to the tallow fatty acid methyl ester distillate used in Example 1, and the resulting mixture was sulfonated according to Example 1 (degree of sulfonation—96%) and bleached. The Klett numbers obtained after a bleaching time of 1 hour at 60° C. with NaOCl as a bleaching agent were 65 (2 percent by weight of NaOCl) and 47 (3 percent by weight of NaOCl), respectively.

EXAMPLE 5

An amount of 2 percent by weight of palmitic acid monoglyceride was added to the tallow fatty acid methyl ester distillate used in Example 1, and this mixture was sulfonated in accordance with the procedure of Comparison Example 1 (degree of sulfonation—96%). The Klett numbers obtained after a bleaching time of 1 hour at 60° C. with NaOCl as a bleaching agent were 42 (2 percent by weight of NaOCl) and 30 (3 percent by weight of NaOCl), respectively.

EXAMPLE 6

As in Example 5, 3 percent by weight of a mixture of oleic acid mono-, di-, and triglyceride, which additionally contained about 10 percent and 1 percent, respectively, of the corresponding glycerides of linoleic acid, were added to the tallow fatty acid methyl ester distillate used in Example 1, and this product mixture was hardened to an iodine number of less than 0.1. After sulfonation, as described in Example 1 (degree of sulfonation—96%), and bleaching with NaOCl, a bleaching time of 1 hour, Klett numbers of 36 (2 percent by weight of NaOCl) and 23 (3 percent by weight of NaOCl), respectively, were obtained.

COMPARISON EXAMPLE 4

As in Example 6, 3 percent by weight of a mixture of ricinoleic mono-, di-, and triglyceride were added to the tallow fatty acid methyl ester distillate used in Example 1, and this product mixture was hardened to an iodine number of less than 0.1. After sulfonation, as described in Example 1 (degree of sulfonation—93%), and bleaching with NaOCl, a bleaching time of 1 hour, Klett numbers of 425 (2 percent by weight of NaOCl) and 270 (3 percent by weight of NaOCl), respectively, were obtained.

COMPARISON EXAMPLE 5

For 6 hours air at 100° C. was conducted through a mixture of oleic mono-, di-, and triglyceride, such as that used in Example 6, which mixture also contained 10 percent and 1 percent of the corresponding glycerides of linoleic acid and linolenic acid, respectively. The hydroxyl number of the mixture thus increased from 220 to 240.

An amount of 3 percent by weight of this mixture was added, as in Example 6, to the tallow fatty acid methyl ester distillate used in Example 1, and this product mixture was hardened (iodine number: 0.05; acid number: 1.4; hydroxyl number: 7.0; saponification number: 196). After sulfonation, as described in Comparison Example 1 (degree of sulfonation—96%) and bleaching with NaOCl, a bleaching time of 1 hour, Klett numbers of 180 (2 percent by weight of NaOCl) and 130 (3 percent by weight of NaOCl), were obtained.

COMPARISON EXAMPLE 6

Tallow fatty acid methyl ester, obtained by re-esterification of tallow with methanol, with subsequent distillation, and hardening, was used as charging material. The material had the following characteristics:

Iodine number: 0.3
Hydroxyl number: 1.1
acid number: 0.5
Saponification number: 195.8

An amount of 42.9 kg per hour of the above material was sulfonated continuously in a fall film reactor with 5 percent by volume of $SO_3$/air and an $SO_3$/ester ratio of 1.2:1 at 90° C. for about 25 minutes (degree of sulfonation—90.4%), neutralized in a pH range of from 6 to 9 with soda lye, and bleached with 3 percent by weight of NaOCl (calculated as 100% and based upon the sulfonated product) for 4 hours at 60° C. The Klett number of the neutral ester sulfonate paste was 95 (5% ester sulfonate solution, blue filter, pH 7).

EXAMPLE 7

Four tons of the charging material used for Comparison Example 6 were distilled additionally up to a sump temperature of 250° C./1 mbar. The distillation residue was about 3 percent by weight.

The distilled material was sulfonated continuously according to the procedure of Comparison Example 6 (degree of sulfonation—96%), and bleached with 2.7 percent by weight of NaOCl. After a bleaching time of 4 hours, the Klett number of the neutral ester sulfonate paste (30%) was 40 (5% ester sulfonate solution, blue filter, pH 7).

EXAMPLE 8

An amount of 42.9 kg per hour of the charging material used for the sulfonation in Example 7 were sulfonated as described therein. The crude sulfonic acid was pre-bleached with 2.86 percent by weight of hydrogen peroxide solution (1 percent by weight, calculated as 100%) and then neutralized and bleached again with 1 percent by weight of NaOCl (calculated as 100%, based upon the material to be sulfonated). The Klett number of the neutral ester sulfonate paste (29%) was 50 (5% ester sulfonate solution, blue filter, pH 7).

As can be seen from the above examples, the presence of fatty acid glycerides in the sulfonation stage is not necessarily harmful. If glycerides of unreacted fatty acids, for example, saturated fatty acids, are added to the material to be sulfonated, there is no additional impairment of the Klett dye number, but added traces of the glycerides of ricinoleic acid or of hydroxystearic acid have a highly discoloring effect. A possible explanation for the effects of the proposal according to the invention could possibly be that when natural fatty acid sources are used, as they are provided according to the invention, minor oxidation processes have taken place, particularly on unsaturated fatty acid molecules, as part of the rancidity of the starting material. The portion of the rancid material is extremely low, percentage wise, but it may be highly noticeable in the sulfonation stage. The removal of the entrained glyceride fraction permits a disproportionally favorable influence on the discoloration in the sulfonation stage. It is thus only these portions in the glyceride compounds carried over from the starting material which have a disturbing effect. The measured addition or presence of color-stable glycerides has no disturbing effect in the sense of the process of the invention.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. In a process for preparing light-colored, wash-active α-sulfofatty acid esters by (a) producing fatty acid esters by (i) re-esterifying fats or oils of vegetable and/or animal origin containing fatty acids having from 6 to 28 carbon atoms with alcohols having from 1 to 8 carbon atoms or (ii) saponifying and esterifying said fats or oils with said alcohols; (b) separating from the reaction mixture of step (a) a fatty acid ester fraction comprising the fatty acid esters formed and accompanying fatty acid glycerides; (c) hydrogenating the fatty ester fraction separated in step (b); (d) sulfonating the fatty acid ester fraction from step (c) to produce sulfonated fatty acid esters; and (e) bleaching the sulfonated fatty acid esters from step (d), the improvement whereby the fatty acid ester fraction from step (b) or (c) is treated to reduce the content of accompanying fatty acid glycerides to 1 percent by weight or less, based upon the weight of the fatty acid ester fraction to be sulfonated, prior to step (c) or (d), respectively.

2. The process of claim 1, wherein the residual content of the accompanying glycerides is reduced to about 0.5 percent by weight or less.

3. The process of claim 2, wherein the residual content of the accompanying glycerides is reduced to about 0.3 percent by weight or less.

4. The process of claim 1, wherein a fatty acid ester fraction with a content of accompanying glycerides of from about 2 to 5 percent by weight is obtained in step (b) by distillation and said fatty acid ester fraction is subjected to a second distillation to reduce the content of accompanying glycerides.

5. The process of claim 4, wherein said fatty acid ester fraction has an accompanying glycerides content of from about 2 to 3 percent by weight.

6. The process of claim 4, wherein the second distillation of the fatty acid ester fraction is effected by overhead distillation up to a sump temperature of about 280° C/1 mbar.

7. The process of claim 1, wherein the sulfonation is effected with a degree of sulfonation of at least 92%.

8. The process of claim 7, wherein the sulfonation is effected with a degree of sulfonation of at least 95%.

9. The process of claim 1, wherein in step (e) the product from step (d) is subjected to bleaching with $H_2O_2$ or $H_2O_2$-supplying compounds and/or sodium hypochlorite to prepare products with a Klett dye number of 60 or less, by either (1) a combination bleaching effected with $H_2O_2$ treatment in the acid range and subsequent sodium hypochlorite treatment in a pH-range of from about 6.5 to 10 or (2) a hypochlorite treatment in a pH-range of from about 6.5 to 10.

10. The process of claim 9, wherein the Klett dye number is 50 or less.

11. The process of claim 9, wherein in the combination bleaching (1) about 1.5 percent by weight or less of $H_2O_2$, calculated as 100% $H_2O_2$, based upon the sulfonated material, as well as about 3 percent by weight or less of hypochlorite are used.

12. The process of claim 11, wherein about 1 percent by weight or less of $H_2O_2$ is used.

13. The process of claim 11, wherein sodium hypochlorite is used.

14. The process of claim 11, wherein about 1 percent by weight or less of hypochlorite is used.

15. The process of claim 9, wherein the bleaching is effected exclusively with up to about 5 percent by weight of hypochlorite, based upon the sulfonated material.

16. The process of claim 15, wherein the hypochlorite is sodium hypochlorite.

17. The process of claim 15, wherein from about 0.1 to 3 percent by weight of hypochlorite is used.

18. The process of claim 9, wherein the hypochlorite bleaching is effected at temperatures of from about 50° to 70° C. with a bleaching time of from about 1 to 10 hours.

19. The process of claim 18, wherein the bleaching is effected at temperatures of from about 55° to 65° C.

20. The process of claim 18, wherein the bleaching time is from about 2 to 4 hours.

21. The process of claim 1, wherein the fatty acid ester fraction from step (c) is treated to reduce the content of accompanying glycerides prior to step (d).

22. The process of claim 1, wherein fatty acid ester fractions with an iodine number less than 1 are sulfonated in step (d).

23. The process of claim 22, wherein the iodine number is less than 0.5.

24. The process of claim 1, wherein aqueous, neutralized ester sulfonate pastes with a wash-active substance content greater than about 28 percent by weight are produced.

25. The process of claim 24, wherein the wash-active substance content is from about 30 to 40 percent by weight.

26. The process of claim 1, wherein hardened tallow fatty acid methyl esters and/or hardened palm oil fatty acid methyl esters are sulfonated in step (d).

27. The process of claim 1, wherein the fatty acid ester fraction from step (b) is treated to reduce the content of accompanying glycerides prior to step (c).

28. The process of claim 1, wherein step (a) comprises re-esterification of said fats or oils with said alcohols.

29. The process of claim 1, wherein step (a) comprises saponification and esterification of said fats or oils with said alcohols.

30. In a process for preparing light-colored, wash-active α-sulfofatty acid esters by (a) producing fatty acid esters by (i) re-esterifying fats or oils of vegetable and/or animal origin containing fatty acids having from 6 to 28 carbon atoms with alcohols having from 1 to 8 carbon atoms or (ii) saponifying and esterifying said fats or oils with said alcohols; (b) separating from the reaction mixture of step (a) a fatty acid ester fraction comprising the fatty acid esters formed and accompanying fatty acid glycerides; (c) sulfonating the fatty acid ester fraction from step (b) to produce sulfonated fatty acid esters; and (d) bleaching the sulfonated fatty acid esters from step (c), the improvement whereby the fatty acid ester fraction from step (b) is treated to reduce the content of accompanying fatty acid glycerides to 1 percent by weight or less, based upon the weight of the fatty acid ester fraction to be sulfonated, prior to step (c).

31. The process of claim 30, wherein the residual content of the accompanying glycerides is reduced to about 0.5 percent by weight or less.

32. The process of claim 31, wherein the residual content of the accompanying glycerides is reduced to about 0.3 percent by weight or less.

33. The process of claim 30, wherein a fatty acid ester fraction with a content of accompanying glycerides of from about 2 to 5 percent by weight is obtained in step (b) by distillation and said fatty acid ester fraction is subjected to a second distillation to reduce the content of accompanying glycerides.

34. The process of claim 33, wherein said fatty acid ester fraction has an accompanying glycerides content of from about 2 to 3 percent by weight.

35. The process of claim 33, wherein the second distillation of the fatty acid ester fraction is effected by overhead distillation up to a sump temperature of about 280° C./1 mbar.

36. The process of claim 30, wherein the sulfonation is effected with a degree of sulfonation of at least 92%.

37. The process of claim 36, wherein the sulfonation is effected with a degree of sulfonation of at least 95%.

38. The process of claim 30, wherein the step (d) the product from step (c) is subjected to bleaching with $H_2O_2$ or $H_2O_2$-supplying compounds and/or sodium hypochlorite to prepare products with a Klett dye number of 60 or less, by either (1) a combination bleaching effected with $H_2O_2$ treatment in the acid range and subsequent sodium hypochlorite treatment in a pH-range of from about 6.5 to 10 or (2) a hypochlorite treatment in a pH-range of from about 6.5 to 10.

39. The process of claim 38, wherein the Klett dye number is 50 or less.

40. The process of claim 38, wherein in the combination bleaching (1) about 1.5 percent by weight or less of $H_2O_2$, calculated as 100% $H_2O_2$, based upon the sulfonated material, as well as about 3 percent by weight or less of hypochlorite are used.

41. The process of claim 40, wherein about 1 percent by weight or less of $H_2O_2$ is used.

42. The process of claim 40, wherein sodium hypochlorite is used.

43. The process of claim 40, wherein about 1 percent by weight or less of hypochlorite is used.

44. The process of claim 38, wherein the bleaching is effected exclusively with up to about 5 percent by weight of hypochlorite, based upon the sulfonated material.

45. The process of claim 44, wherein the hypochlorite is sodium hypochlorite.

46. The process of claim 44, wherein from about 0.1 to 3 percent by weight of hypochlorite is used.

47. The process of claim 38, wherein the hypochlorite bleaching is effected at temperatures of from about 50° to 70° C. with a bleaching time of from about 1 to 10 hours.

48. The process of claim 47, wherein the bleaching is effected at temperatures of from about 55° to 65° C.

49. The process of claim 47, wherein the bleaching time is from about 2 to 4 hours.

50. The process of claim 30, wherein fatty acid ester fractions with an iodine number less than 1 are sulfonated in step (c).

51. The process of claim 50, wherein the iodine number is less than 0.5.

52. The process of claim 30, wherein aqueous, neutralized ester sulfonate pastes with a wash-active substance content greater than about 28 percent by weight are produced.

53. The process of claim 52, wherein the wash-active substance content is from about 30 to 40 percent by weight.

54. The process of claim 30, wherein hardened tallow fatty acid methyl esters and/or hardened palm oil fatty acid methyl esters are sulfonated in step (c).

55. The process of claim 30, wherein step (a) comprises re-esterification of said fats or oils with said alcohols.

56. The process of claim 30, wherein step (a) comprises saponification and esterification of said fats or oils with said alcohols.

* * * * *

UNITED STATES PATENT AND TRADEMARK OFFICE
CERTIFICATE OF CORRECTION

PATENT NO. : 4,671,900

DATED : June 9, 1987

INVENTOR(S) : KARL SCHMID et al.

It is certified that error appears in the above-identified patent and that said Letters Patent is hereby corrected as shown below:

Col. 1, line 17, "mineral" should read -- animal --.

Col. 2, line 22, "of" should read -- or --.

Col. 2, lines 29-30, "purifications" should read -- purification --.

Col. 2, line 43, "difficulties" should read -- difficulties, --.

Col. 6, line 26, "acid" should read -- sulfonic acid --.

Col. 6, line 30, "soluton" should read -- solution --.

Col. 8, line 27, "alochols" should read -- alcohols --.

Col. 8, line 62, "=" should read -- $\hat{=}$ --.

Col. 8, line 65, "=" should read -- $\hat{=}$ --.

Col. 15, Claim 38, line 1 thereof, "the step" should read -- in step --.

Signed and Sealed this

Twenty-seventh Day of October, 1987

Attest:

DONALD J. QUIGG

*Attesting Officer*    *Commissioner of Patents and Trademarks*